United States Patent [19]

Varma et al.

[11] 4,421,820

[45] Dec. 20, 1983

[54] ELASTOMER-MODIFIED PHOSPHORUS-CONTAINING IMIDE RESINS

[75] Inventors: Indra K. Varma, New Delhi, India; George M. Fohlen, Millbrae; John A. Parker, Los Altos, both of Calif.

[73] Assignee: The United States of America as represented by the Administrator of the National Aeronautics and Space Administration, Washington, D.C.

[21] Appl. No.: 441,899

[22] Filed: Nov. 15, 1982

[51] Int. Cl.³ .................. C08K 3/04; C08K 3/40; B32B 7/00; D03D 3/00
[52] U.S. Cl. .................. 428/246; 524/494; 524/496; 524/500; 524/530; 525/282; 525/287; 428/260; 428/367; 428/408; 428/473.5; 428/902; 428/920
[58] Field of Search ........... 524/500, 530, 494, 490; 428/260, 246, 473.5, 367, 408, 902, 920; 525/282, 287

[56] References Cited

U.S. PATENT DOCUMENTS

| | | | |
|---|---|---|---|
| 4,088,708 | 5/1978 | Riew | 525/113 |
| 4,094,911 | 6/1978 | Mitsch et al. | 528/42 |
| 4,238,528 | 12/1980 | Angelo et al. | 524/600 |
| 4,276,344 | 6/1981 | Frosch et al. | 428/260 |

OTHER PUBLICATIONS

Clair et al., Sampe Technical Conf., Oct. 7-9, 1980, pp. 729-737.
Adv. in Chem Series No. 129, Webster et al., pp. 61-79 (1973).

*Primary Examiner*—John C. Bleutge
*Assistant Examiner*—Herbert J. Lilling
*Attorney, Agent, or Firm*—Darrell G. Brekke; John R. Manning

[57] ABSTRACT

Phosphine oxide-containing polyimide resins modified by elastomers, having improved mechanical properties and particularly useful in the production of fiber or fabric-reinforced composites or laminates.

9 Claims, 1 Drawing Figure

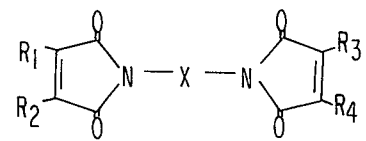
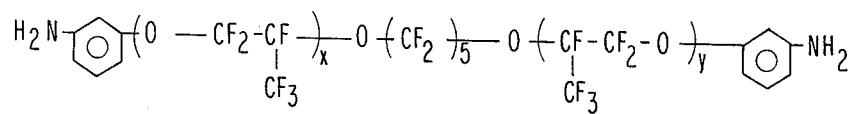
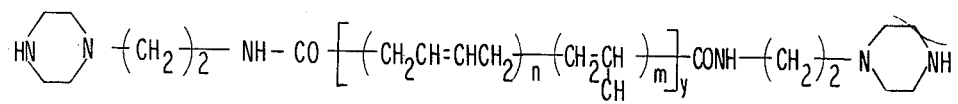

ELASTOMER-MODIFIED PHOSPHORUS-CONTAINING IMIDE RESINS

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

FIELD OF THE INVENTION

This invention relates to phosphorus-containing polyimide resins modified by elastomers. More specifically, this invention relates to phosphorous-containing polyimide resins modified by amine group-terminated elastomers, where the modified resins have improved mechanical properties and are particularly useful in the production of fiber or fabric-reinforced composites or laminates.

BACKGROUND OF THE INVENTION

Alteration of the mechanical properties of resins is often desired and improvement of the mechanical properties of epoxy resins by way of the addition of reactive butadiene-acrylonitrile copolymers has been extensively investigated. Improvements in flexural strength in such modified resins and in the toughness of carbon fiber composites made therefrom has been reported (See Gilwee et al., "Proceedings, National Symposium on Polymers in the Service of Man", Washington, D.C. (June 9-11, 1980)). Improvement in the fracture toughness of LARC-13, a high temperature addition polyimide adhesive, by use of an amine-terminated butadiene-acrylonitrile elastomer has also been reported (See St. Clair et al., "Proceedings, 12th National SAMPE Technical Conference", p. 729 (October 1980)). The preparation and characteristics of phosphorus-containing imide resins (See Varma et al., U.S. Pat. No. 4,276,344 and U.S. Pat. No. 4,395,557 and perfluoroethylene ether diamine (See Webster et al., Adv. in Chem. Series, No. 129, p. 61 (1973)) have been described. Further, the reaction of maleic acid imides with amines is also known (See Bargain et al., U.S. Pat. No. 3,562,223).

Even though improvements have been obtained in the nature of various resins by appropriate modifications as described in the prior art, it is desired to further improve the nature of and mechanical properties of resins.

SUMMARY OF THE INVENTION

An object of this invention is to provide novel elastomer modified phosphorus-containing resins.

A further object of this invention is to provide resins comprising the reaction product of amine-terminated elastomers and phosphorus-containing resins as a matrix.

An even further object of this invention is to provide amine-terminated elastomer modified phosphorus-containing matrix resins having improved mechanical properties.

An additional object of this invention is to provide elastomer modified phosphorus-containing imide resins particularly suitable for structural applications arising as a result of their improved and excellent mechanical properties.

Accordingly, in one embodiment, this invention provides a thermosetting resin comprising the reaction product of (1) a phosphorus-containing N,N'-bisimide of an unsaturated carboxylic acid of the formula (I)

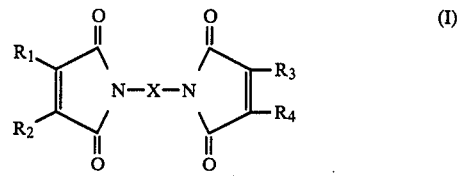

wherein $R_1$, $R_2$, $R_3$ and $R_4$, which may be the same or different, each represents a hydrogen atom, a lower alkyl group (e.g., methyl, ethyl, propyl, etc.) or a halogen atom (such as chlorine or bromine) and X is a divalent aromatic organic group containing a phosphine oxide moiety;
with (2) a di(amino group-terminated) elastomer of low molecular weight, e.g., a molecular weight of about 6000 or less, such as a di(amino group-terminated)perfluoroalkylene ether or a di(amino group-terminated)-butadiene-acrylonitrile copolymer.

BRIEF DESCRIPTION OF THE ACCOMPANYING DRAWING

The FIGURE shows structurally the N,N'-bisimide (1) and embodiments of low molecular weight di(amino group-terminated) elastomers (2) used to produce the elastomer-modified imide resin of this invention.

DETAILED DESCRIPTION OF THE INVENTION

As indicated above, the elastomer-modified phosphorus-containing imide resin of this invention is a thermosetting resin and comprises the reaction product of (1) a phosphine oxide moiety containing N,N'-bisimide of an unsaturated dicarboxylic acid of the formula (I) above with (2) a di(amino group-terminated)elastomer, whereby the mechanical properties, particularly toughness, of the resin obtained are improved.

As indicated above, $R_1$, $R_2$, $R_3$ and $R_4$ may be the same or different and each can represent a hydrogen atom, a lower alkyl group such as a methyl group, an ethyl group, a propyl group, etc., or a halogen atom such as a chlorine atom or a bromine atom, preferably a hydrogen atom or a methyl group.

X in formula (I) above basically represents a divalent aromatic group linking the two imide rings which also contains a phosphine oxide moiety in the chain of the linking group or as a pendant group on the linking group, preferably in the chain of the linking group. Basically, any divalent aromatic linking group which can contain a phosphine oxide moiety in or on the chain thereof which links the two imide rings can be employed. In particular, suitable examples of divalent aromatic ring-containing linking groups for X which also contain a phosphine oxide moiety in or on the chain thereof include, for example,

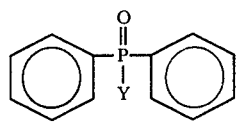

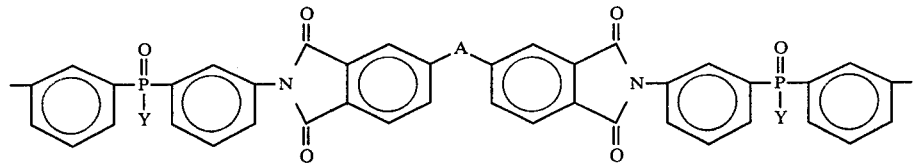

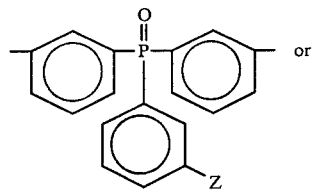

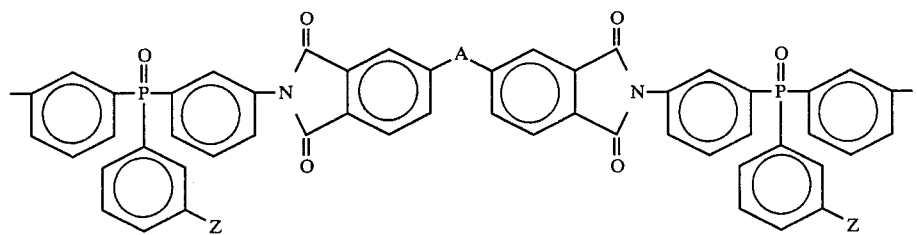

where Z in the above formulas can also be in the para-position, and wherein in the above divalent groups, Y represents a lower alkyl group having 1 to 5 carbon atoms (such as a methyl group, an ethyl group, etc.) or a phenyl group;

Z represents an amino group or alternatively an imide ring of the formula

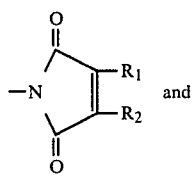

and

A represents

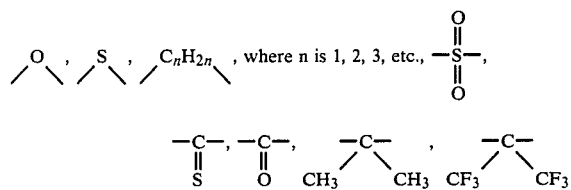

or any other divalent group.

The phosphine oxide moiety containing N,N'-bisimide of an unsaturated dicarboxylic acid of the formula (I) can be prepared in accordance with the disclosure contained in Varma et al., U.S. Pat. No. 4,276,344, and U.S. Pat. No. 4,395,557 the disclosure of which is incorporated herein by reference, for example, by reaction of a phosphorus-containing aromatic diamine with an unsaturated cyclic anhydride such as maleic anhydride to produce the bisimide. By following the procedures as described in U.S. Pat. No. 4,276,344 and U.S. Pat. No. 4,395,557 filed July 30, 1981, and choosing the appropriate phosphorus-containing aromatic diamine and the appropriate cyclic anhydride, phosphine oxide moiety containing N,N'-bisimides of unsaturated dicarboxylic acids within the scope of the formula (I) above can be appropriately prepared. Basically in this reaction, the monoimide is first formed and the bisimide can be subsequently formed by further reaction with additional cyclic anhydride or alternatively by conducting the reaction in the presence of excess cyclic anhydride for a sufficient period of time the bisimide is formed.

Suitable examples of cyclic anhydrides which can be used include maleic anhydride, dichloromaleic anhydride, citraconic anhydride along with other substituted maleic anhydrides in which the hydrogen atoms thereof, corresponding to the $R_1$-$R_4$ positions, are replaced by lower alkyl groups, e.g., having one to four carbon atoms or halogen atoms, preferably chlorine or bromine.

Also up to 50% on a molar basis of the cyclic anhydride described above can be replaced by benzophenone tetracarboxylic dianhydride, or 2,2-bis(3,4-dicarboxyphenyl)hexafluoropropane dianhydride, if desired, to achieve additional properties.

The phosphine oxide component of the bisimides used as a starting material in U.S. Pat. No. 4,276,344 can be produced by the method of Arbuzov et al., Zh. Obshch. Khim., 18, 2008 (1948), involving the reaction of a triarylphosphine such as triphenylphosphine with methyl iodide followed by treatment with potassium hydroxide, nitration and reduction of the nitro groups to amino groups. Further, the process for making bisimides from phosphine oxide moiety containing compounds similar to those set forth above is disclosed in U.S. Pat. No. 2,444,536.

The production of the bisimides is preferably conducted in a polar solvent such as N,N-dimethylformamide, acetone, N-methylpyrolidone, etc., wherein the phosphine oxide containing diamine and the cyclic anhydride components are employed in substantially stoichiometric proportions although an excess of up to 10% of either component may be employed if desired.

Suitable specific examples of phosphine oxide moiety containing N,N'-bisimides of unsaturated dicarboxylic acids of the formula (I) include:

3,3'-bis(maleimidophenyl)methylphosphine oxide,
3,3'-bis(citraconimidophenyl)methylphosphine oxide,
3,3'-bis(dichloromaleimidophenyl)methylphosphine oxide,
3,3'-bis(maleimidophenyl)-3''-aminophenylphosphine oxide,
3,3'-bis(citraconimidophenyl)-3''-aminophenylphosphine oxide,
3,3'-bis(dichloromaleimidophenyl)-3''-aminophenylphosphine oxide,
3,3',3''-tris(maleimidophenyl)phosphine oxide,
3,3',3''-tris(citraconimidophenyl)phosphine oxide and
3,3',3''-tris(dichloromaleimidophenyl)phosphine oxide.

Preferred examples of these compounds of the formula (I) include 3,3'-bis(maleimidophenyl)-3''-aminophenyl phospine oxide, and

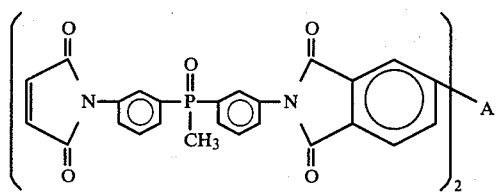

where A is >CO, >C(CF$_3$)$_2$, or >SO$_2$.

The second component used to prepare the elastomer-modified phosphorus-containing imide resins of the present invention is a low molecular weight di(amino group-terminated) elastomer such as a di(amino group-terminated)perfluoroalkylene ether (such as perfluoromethylene, perfluoroethylene, perfluoroisopropylene, etc.) or a di(amino group-terminated)butadiene-acrylonitrile copolymer.

More specifically, one embodiment of the di(amino group-terminated)perfluoroalkylene ether elastomer can be represented by the formula

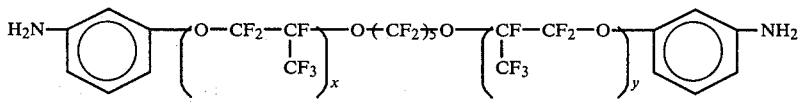

wherein x+y=2 or 3 and the di(amino group-terminated)butadiene-acrylonitrile copolymer can be represented by the formula

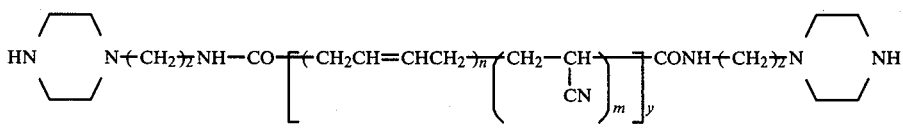

wherein m represents 1 and n represents 5 and y=10 (approximately).

Hereinafter for simplicity, the di(amino group-terminated)perfluoroalkylene ether will be designated PFAE and the di(amino group-terminated)butadiene-acrylonitrile copolymer will be designated ATBN. PFAE and ATBN are well known in the art. ATBN is commercially available and PFAE can be prepared as described in Webster et al, supra.

Elastomer-modified phosphorus-containing imide resins of this invention, as indicated above, are the reaction product of (1) a phosphine oxide moiety containing N,N'-bisimide of an unsaturated dicarboxylic acid of the formula (I) and (2) a di(amino group-terminated)elastomer as described above. The reaction of the di(amino group-terminated)elastomer with the imide of the formula (I) can be carried out in an inert polar solvent such as N,N-dimethylformamide, N-methylpyrrolidone or N,N-dimethylacetamide. A suitable temperature for the reaction can range from 20° C. to 30° C. and a suitable period of time for reaction can range from about 12 hours to about 20 hours. The concentration of the amine-terminated elastomer and the imide in the inert polar solvent can suitably range from about 0.5 to 4% by weight and 25 to 35% by weight, respectively.

In order to achieve an improvement in the mechanical properties of the imide resins by modification thereof by reaction with the amine terminated elastomer, an appropriate percent by weight modification of the imide resin by the elastomer can range from about 3% to about 10% by weight based on the weight of the imide (1) used.

The elastomer-modified bisimide resins in accordance with this invention can be appropriately cured and thereby cross-linked at temperatures, preferably within the range of about 180° C. to about 220° C.

The elastomer-modified resins of this invention have a wide variety of applications, particularly where good adhesion, excellent resistance to heat, fire, solvents and chemicals, and strong and tough mechanical properties are required. In particular, the elastomer-modified resins of this invention can be advantageously employed as adhesives and as a matrix resin material for fiber-reinforced lightweight composites.

Appropriate fibrous reinforcing materials which can be used include graphite fibers and graphite cloth, glass fibers and carbon fibers.

In order to illustrate the present invention in greater detail, reference is made to the following examples thereof.

These examples are given merely for the purpose of illustration and are not to be construed as limiting the present invention. In these examples, the test methods employed were carried out in accordance with the following standard test methods.

| | |
|---|---|
| Flexural Test | ASTM D790-63 |
| Tensile Test | ASTM D638 |
| Short Beam Shear | ASTM D2344 |
| Limiting Oxygen Index | ASTM D2863 |

EXAMPLE 1

A bisimide involving tris(m-aminophenylphosphine oxide) was prepared by reacting 24.225 g of tris(m-aminophenyl)phosphine oxide (0.075 mole) with 15.68 g of maleic anhydride (0.16 mole) in 90–100 ml of dimethylformamide. The solution was stirred at room temperature (about 25°–30° C.) for one hour and then refluxed for 1-2 hrs. The solution was then cooled and 2.6 g of ATBN was added. The mixture was then stirred at room temperature overnight.

Eight plies of graphite cloth (8-harness satin weave cloth) were brush coated with this solution and these prepregs were dried at 125±5° C. for 20-30 mins. After the thus produced impregnated prepregs were stacked together, curing of the assembly was done at 180° C. at a pressure of 140 psi for 2½ hr. Post-curing was accomplished at 218±2° C. for 16 hr. Using the test methods above, the shear strength of a laminate containing 26.6% resin was $5.85 \times 10^3$ psi, the tensile strength was $61.91 \times 10^3$ psi, the flexural strength was $149.62 \times 10^3$ psi and the flexural modulus was $25.21 \times 10^6$ psi. This indicates an improvement of 98.9%, 35.2%, 96.8% and 17.7%, respectively, over using the same procedures of impregnation of eight plies of graphite cloth with the bisimide resin unmodified with ATBN and assembly thereof into a laminate.

EXAMPLE 2

An N,N-dimethylformamide solution of the bisimide as in Example 1 was prepared from identical quantities of the same reactants as described in Example 1 above. To this solution, 1.44 g of ATBN was added and, after stirring the solution at room temperature for several hours, the solution was used to fabricate a graphite cloth laminate using the same procedures as in Example 1. A laminate with 28.9% resin had a shear strength of $3.58 \times 10^3$ psi (21.8% improvement), a tensile strength of $49.18 \times 10^3$ psi (7.4% improvement), a flexural strength of $88.70 \times 10^3$ (16.6% improvement) and a flexural modulus of $16.3 \times 10^6$, the improvement being as to a control laminate as in Example 1.

EXAMPLE 3

An N,N-dimethylformamide solution of a bisimide as in Example 1 was prepared from identical quantities of the same reactants as described in Example 1. To this solution, 2.34 g of perfluoroethylene ether diamine was added and the solution was stirred at room temperature overnight. A graphite cloth laminate fabricated as described using the procedures of Example 1 had a limiting oxygen index of 100, a shear strength of $5.95 \times 10^3$ psi and a tensile strength of $48.4 \times 10^3$ psi. The resin content of the laminate was 24.2%. This indicates an improvement of 105.4%, and 5.7% in shear strength and tensile strength, respectively, as to a control laminate.

EXAMPLE 4

24.6 g (0.1 mole) of bis(m-aminophenyl)methylphosphine oxide was dissolved in N,N-dimethylformamide and 10.78 g (0.11 mole) of maleic anhydride was added. The solution was stirred at room temperature and then 16.1 g (0.05 mole) of benzophenone tetracarboxylic acid dianhydride was added. After the solution had been stirred at room temperature for several hours, it was refluxed for 1 to 2 hours. After cooling the solution, 2.95 g of perfluoroalkylene ether diamine PFAE was added. The solution was stirred overnight at room temperature and a graphite cloth laminate as described in Example 1 (8 plies) was fabricated by curing at 232° C. for 90 mins. followed by post-curing at 280° C. for 70 mins. A laminate with a resin content of 22.5% had a limiting oxygen index of 100, a shear strength of $10.2 \times 10^3$ psi (89.6% improvement), a tensile strength of $76.9 \times 10^3$ psi (28.6% improvement), a flexural strength of $138.64 \times 10^3$ psi (26.7% improvement) and a flexural modulus of $20.04 \times 10^6$ (no change).

The improvement percentages shown for the evaluations above are with respect to a graphite cloth laminate using the same bisimide resin but unmodified with the perfluoroethylene ether diamine.

While the invention has been described in detail and with respect to various embodiments thereof, it will be apparent to one skilled in the art that various changes and modifications can be made therein without departing from the spirit and scope thereof.

We claim:

1. A thermosetting phosphorus-containing imide resin comprising the reaction product of
   (1) a phosphine oxide moiety containing N,N'-bisimide of an unsaturated dicarboxylic acid of the formula (I)

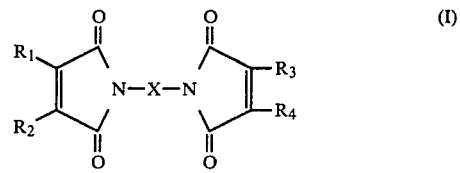

wherein $R_1$, $R_2$, $R_3$ and $R_4$, which may be the same or different, each represents a hydrogen atom, a lower alkyl group or a halogen atom, and X is a divalent aromatic group containing a phosphine oxide moiety;

with (2) a low molecular weight di(amino group-terminated) elastomer wherein the amount of said elastomer to the weight of said N,N'-bisimide of the formula (I) ranges from about 3% to about 10% by weight.

2. The thermosetting resin of claim 1, wherein the N,N'-bisimide of the formula (I) is selected from the group consisting of
   3,3'-bis(maleimidophenyl)methylphosphine oxide,
   3,3'-bis(citraconimidophenyl)methylphosphine oxide,
   3,3'-bis(dichloromaleimidophenyl)methylphosphine oxide,
   3,3'-bis(maleimidophenyl)-3''-aminophenylphosphine oxide,
   3,3'-bis(citraconimidophenyl)-3''-aminophenylphosphine oxide,
   3,3'-bis(dichloromaleimidophenyl)-3''-aminophenylphosphine oxide,
   3,3',3''-tris(maleimidophenyl)phosphine oxide,
   3,3',3''-tris(citraconimidophenyl)phosphine oxide and
   3,3',3''-tris(dichloromaleimidophenyl)phosphine oxide.

3. The thermosetting imide resin of claim 2, wherein up to about 50% on a molar basis of the unsaturated dicarboxylic acid is replaced by benzophenone tetracarboxylic acid dianhydride or 2,2-bis-(3,4-dicarboxyphenyl)hexafluoropropane dianhydride.

4. The thermosetting imide resin of claim 1, wherein said di(amino group-terminated) elastomer is a di(amino group-terminated)perfluoroalkylene ether of the formula

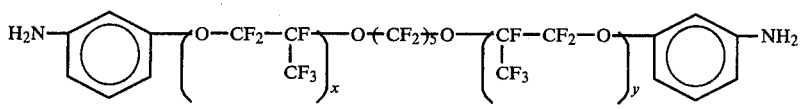

wherein x+y is 2 or 3 or a di(amino group-terminated)-butadiene-acrylonitrile copolymer of the formula

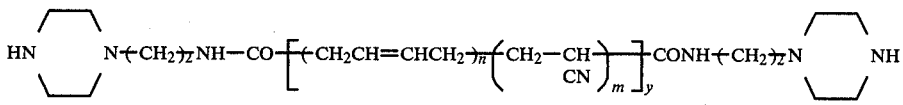

wherein n represents 5 and m represents 1 and y represents 10, approximately.

5. The thermosetting imide resin of claim 1, wherein X is

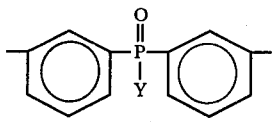

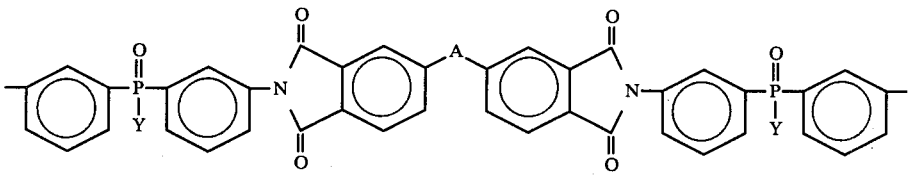

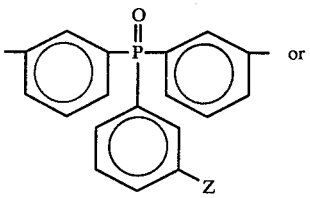

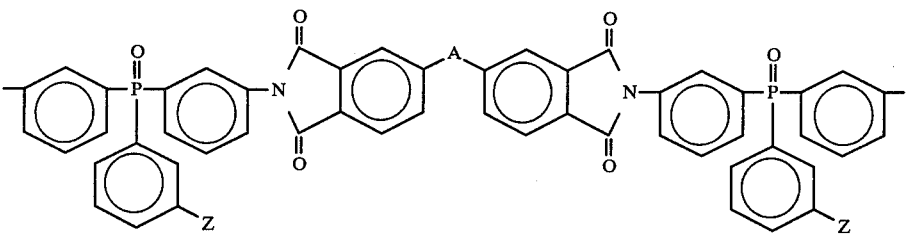

where Z in the above formulas can also be in the para-position, and wherein in the above divalent groups, Y represents a lower alkyl group having 1 to 5 carbon atoms or a phenyl group;

Z represents an amino group or alternatively an imide ring of the formula

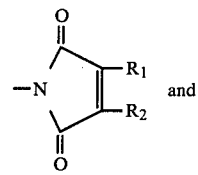

A represents $-\overset{O}{\underset{O}{\overset{\|}{S}}}-$, $-\overset{O}{\underset{\|}{C}}-$, $-\overset{S}{\underset{\|}{C}}-$, $-\overset{CH_3}{\underset{CH_3}{C}}-$, or $-\overset{CF_3}{\underset{CF_3}{C}}-$ 6. A reinforced resin composition comprising the thermosetting phosphorus-containing imide resin of claims 1, 2, 3, 4, or 5 and inorganic fibers as a reinforcing agent.

7. The reinforced resin composition of claim 6, wherein the inorganic fibers are graphite fibers, carbon fibers or glass fibers.

8. The reinforced resin composition of claim 7, wherein the inorganic fibers are graphite fibers in the form of a graphite cloth.

9. A laminate comprising a cured assembly of plies of graphite cloth impregnated with the thermosetting phosphorus-containing imide resin of claim 1, 2, 3, 4 or 5.

* * * * *